United States Patent [19]

West

[11] 4,127,773
[45] Nov. 28, 1978

[54] CHARACTERIZING AND IDENTIFYING MATERIALS
[75] Inventor: Michael A. West, Orpington, England
[73] Assignee: Applied Photophysics Limited, London, England
[21] Appl. No.: 783,114
[22] Filed: Mar. 31, 1977
[51] Int. Cl.² .......................... G01N 21/38; G01J 3/34
[52] U.S. Cl. .................................. 250/461 R; 250/226
[58] Field of Search .............. 250/461 R, 461 B, 568, 250/226, 223, 224, 227; 350/96 B; 235/61.11 E; 307/355, 357, 311; 328/146, 147, 148, 116, 117

[56] References Cited
U.S. PATENT DOCUMENTS

| 3,573,458 | 4/1971 | Anger ................................ 250/71.5 |
| 3,649,118 | 3/1972 | Yano et al. ............................ 355/38 |
| 3,709,612 | 1/1973 | Clemens ............................... 356/178 |
| 3,992,631 | 11/1976 | Harte ................................... 250/365 |

Primary Examiner—Alfred E. Smith
Assistant Examiner—Janice A. Howell
Attorney, Agent, or Firm—Sughrue, Rothwell, Minn, Zinn and Macpeak

[57] ABSTRACT

In characterizing or identifying an article which is provided with luminescent material, excitation radiation is directed at the article to cause emission from the luminescent material and the intensity of emitted radiation at different wavelengths is compared by directing the emitted radiation to photodetectors through a plurality of optical systems having respective filters of different wavelength transmission and comparing the modified signal level from one photodetector with the signal level from another photodetector.

14 Claims, 9 Drawing Figures

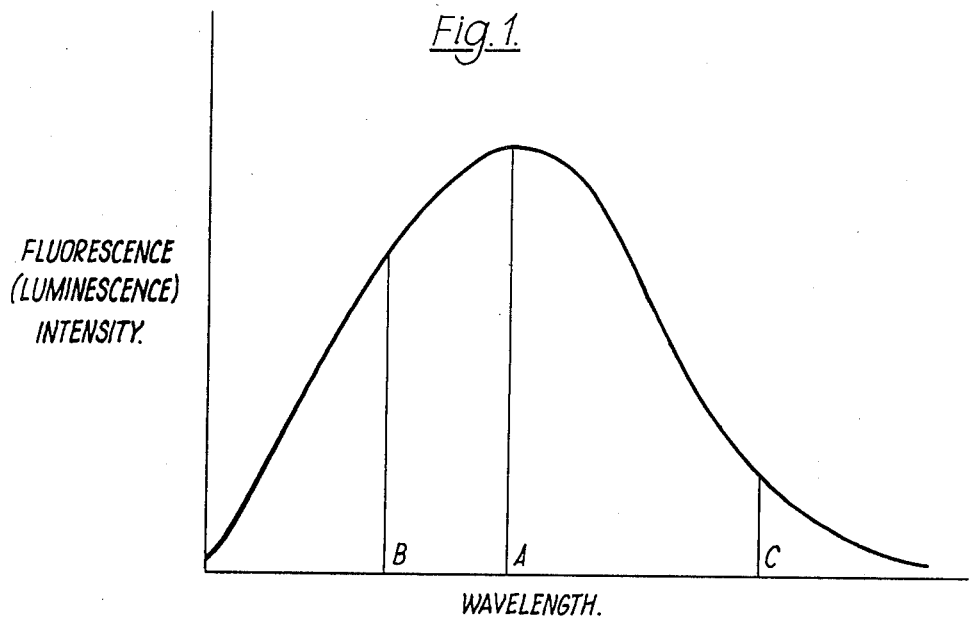
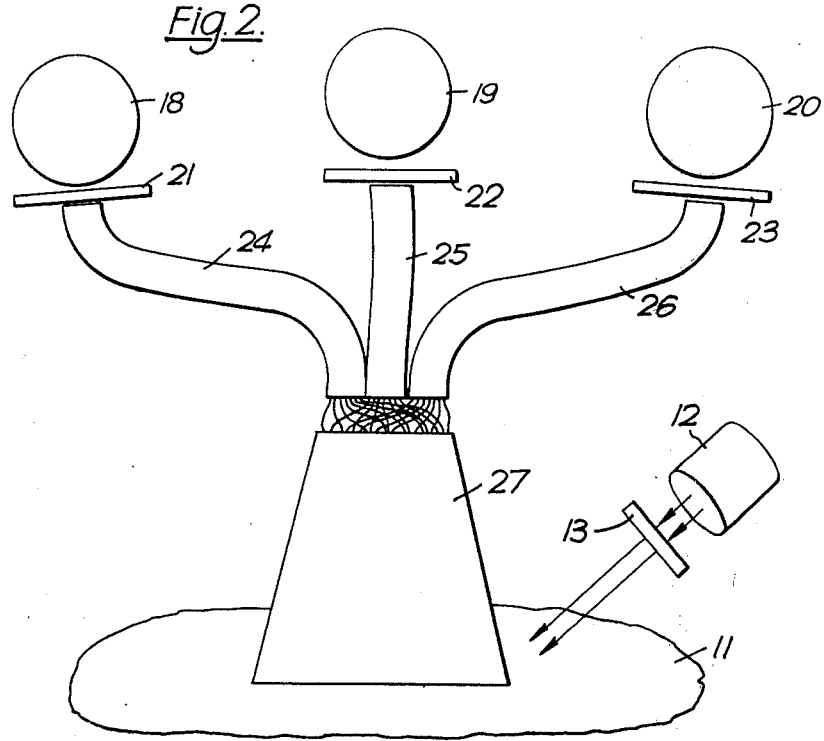

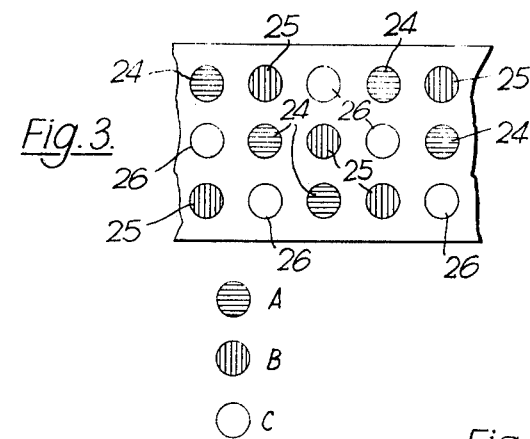
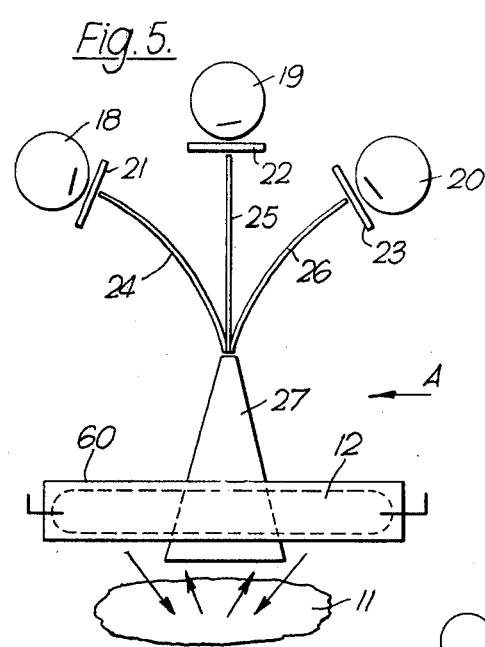
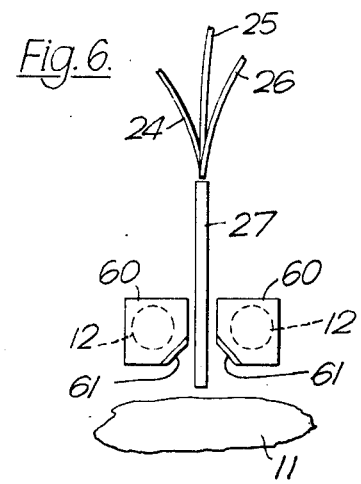
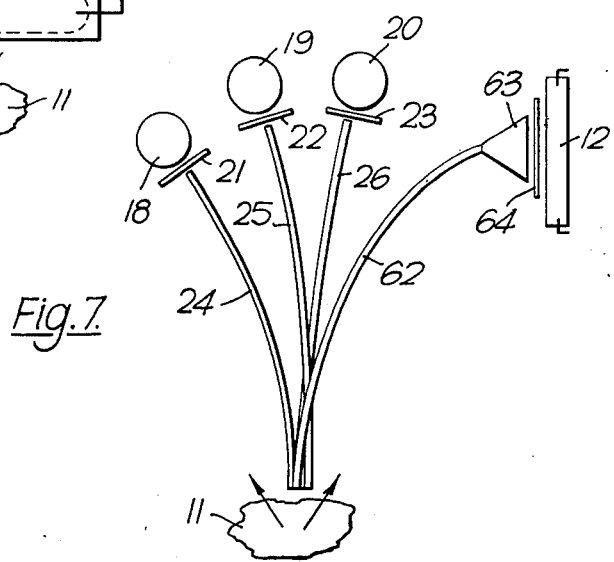

CHARACTERIZING AND IDENTIFYING MATERIALS

BACKGROUND OF THE INVENTION

This invention relates to apparatus and a method for the characterisation and/or identification of an article utilising the properties of a luminescent material incorporated into, or positioned on, said article.

It is known that the emission spectra of luminescent materials can often be unique to a particular compound.

It is an object of the present invention to provide an improved method and apparatus for characterisation and/or identification of articles by examination of the intensity — wavelength distribution in the emission spectrum derived from luminescent material incorporated into or positioned on an article under test.

SUMMARY OF THE INVENTION

The invention provides a method of characterising or identifying an article which incorporates or carries luminescent material, which method comprises directing excitation radiation at the luminescent material on an article under test so as to cause the luminescent material to emit luminescent radiation, detecting the emitted radiation at different wavelengths by simultaneously directing said radiation through a plurality of optical systems to respective photodetectors, each optical system incorporating filter means so as to transmit to its associated photodetector a different selected wavelength or range of wavelengths from that transmitted to another photodetector and each photodetector giving rise to an output signal which varies linearly in level in accordance with the intensity of the emitted radiation incident thereon, modifying the signal level from one photodetector by attenuation or amplification and comparing said modified signal level with the signal level derived from another photodetector.

The invention also provides apparatus for characterising or identifying an article which incorporates or carries luminescent material, which apparatus comprises a source of excitation radiation for directing radiation at the luminescent material when the article is at a test station, a plurality of optical systems arranged to receive simultaneously radiation emitted by the luminescent material and direct the radiation to respective photodetectors, a plurality of optical filters each arranged to transmit a different wavelength and each being located in a respective one of the optical systems and arranged to pass radiation of a selected wavelength or range of wavelengths to the associated photodetector, and electrical circuit means arranged so as (1) to receive electrical output signals derived from said photodetectors, said signals varying in accordance with the intensity of radiation incident thereon; (2) to modify the signal level from one photodetector by attenuation or amplification; (3) to compare the modified signal level with a signal level derived from another photodetector and (4) to indicate when said other signal level bears a predetermined relationship to the modified signal level.

Preferably the photodetectors are arranged to provide output signals which vary linearly in accordance with the intensity of radiation incident thereon.

Preferably the aforesaid electrical circuit means is arranged so as (1) to receive electrical output signals derived from said photodetectors, said signals varying linearly in level in accordance with the intensity of the radiation incident thereon; (2) to modify the signal level from one photodetector to provide two different modified signal levels serving to define a required range; (3) to compare a signal level derived from another photodetector with each of the modified signal levels and (4) to indicate when said signal level derived from said other photodetector is within said required range. In providing the two different modified signal levels, the electrical circuit means may derive both modified signals from the original signal from said one photodetector although preferably the signal level from the one photodetector is used to provide a first modified signal level and said first modified signal level is used to provide the second modified signal level.

Preferably modified signal levels derived from one photodetector are compared with signal levels derived from at least two other photodetectors.

Preferably said optical systems each comprise a bundle of optical fibres, each bundle having one end arranged to direct light to a respective photodetector and the other ends of the fibres forming one or more groups, the or each group having fibres lying closely adjacent each other in a common plane and distributed so that fibres of all bundles have an even distribution at the end arranged to receive radiation from the article under test.

Preferably at least one light pipe is provided for receiving radiation emitted by the luminescent material and directing the radiation to one end of the bundles of fibres. Preferably the fibres of all said bundles are connected at one end to one or more light pipes common to all the bundles, the fibres of the different bundles having an even distribution at the interface with the or each light pipe.

Preferably the source of excitation radiation comprises a radiation source located adjacent at least the end of the fibre bundles arranged to receive radiation emitted by the luminescent material.

An elongated excitation source may be used and light from the source may be directed onto the article under test by use of suitable optic means such as a light pipe, fibre optics, lenses or mirrors.

Additional optical fibres may be provided for directing the excitation radiation from the radiation source onto the luminescent material, said additional fibres being distributed amongst the fibres forming the said optical systems.

The use of one or more common light pipes to direct light emitted by the luminescent material into the bundles of fibres is particularly advantageous in providing even transmission of the emitted radiation to all bundles. It avoids problems that might otherwise arise in achieving uniform transmission into the different bundles of fibres particularly in cases where there is uneven intensity of illumination over the luminescent material being viewed by the fibres. The light pipe or pipes collect all the radiation emitted over the area of luminescent material under view at any instant and this light is then transmitted to the ends of the fibre bundles in an even manner regardless of the intensity distribution over the area of the luminescent material.

Preferably the or each light pipe used to receive radiation emitted by the luminescent material is tapered so that the cross-sectional area of the light pipe is smallest at the interface with the fibre ends.

Preferably the source of excitation radiation is arranged to emit radiation in the ultraviolet wavelength range although in some cases visible light may be used.

The source of excitation radiation may conveniently be in the form of a flash lamp such as a xenon filled flash lamp being operated from a pulsed supply. Alternatively a low pressure mercury lamp operating continuously may be used providing single mercury lines. Phospher coating may be used on the lamp to give broader spectral lines. The excitation radiation may be in single wavelengths or isolated ranges of wavelengths.

It will be understood that the present invention involves the detection of emitted radiation at different wavelengths and forming an assessment of the relative intensities of the emitted radiation at the different wavelengths. This allows positive characterisation or identification of articles carrying the luminescent material due to the unique emission spectra of certain luminescent compounds. It is the shape of the wavelength-intensity emission spectrum which is important and by comparing the relative intensities at separate selected wavelengths, the results obtained are independant of the general intensity of emitted radiation.

The article which carries the luminescent material may comprise any suitable material, such as paper, cardboard, metal, plastics or fabric provided that when incorporated therein, or positioned thereon, the properties of the luminescent material are not significantly affected.

The luminescent material may be incorporated into or positioned upon the article during or after its manufacture. For example, if the article comprises a thermoplastics material, the luminescent material may be incorporated therein during the manufacture of the article by extrusion or moulding. When the article comprises a fibrous material such as paper, cardboard or a textile, the luminescent material may be incorporated therein during the course of preparation of the article, suitably in the form of a fibre or thread comprising the luminescent material. Alternatively the luminescent material may be applied to the article by printing, typing or writing. The luminescent material may or may not be coloured. Optionally it may be utilised alone or in conjunction with coloured dyes or pigments.

By choosing one or more suitable luminescent materials it is possible to fingerprint a particular object on the basis of its characteristic emission spectrum. For example, labels for antibiotic preparations containing details of dosages, potency, age etc. or photographic chemicals of limited shelf life can be marked with appropriate luminescent materials and positively identified by use of the present invention. The labels can also be sorted on the basis of their fluorescent signals.

In addition to label verification and sorting it is possible to determine ageing affects or chemicals affects such as light fading by using materials which have specifically poor chemical stabilities.

BRIEF DESCRIPTION OF THE DRAWINGS

FIG. 1 shows a characteristic emission spectrum from a luminescent material,

FIG. 2 is a diagrammatic view of one embodiment of the invention,

FIG. 3 shows the arrangement of optical fibres used in the embodiment of FIG. 2, FIG. 5 shows the optical arrangement of an alternative embodiment, FIG. 6 is a view in the direction of the arrow A in FIG. 5, FIG. 7 shows the optical arrangement of a further embodiment of the invention.

DESCRIPTION OF THE PREFERRED EMBODIMENTS

Figure 4:
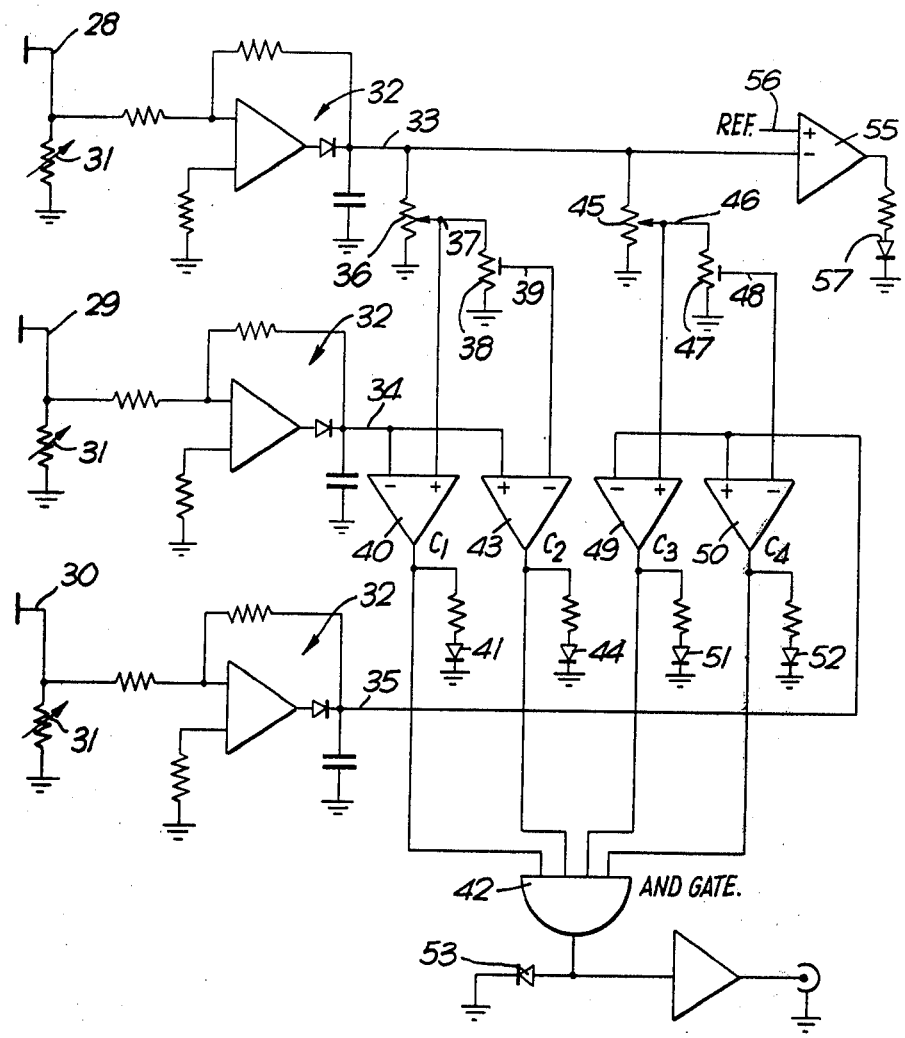
FIG. 4 shows the control circuits used with the embodiment of FIG. 2.

The examples described below all relate to the characterisation or identification of articles bearing luminescent material which provides a characteristic emission spectrum. FIG. 1 shows diagrammatically a simple form of emission spectrum which can be obtained from a luminescent material. The luminescent materials used with the present invention are selected so that the shape of the wavelength — intensity spectrum is characteristic of the luminescent material and unique for that material. The intensity of radiation emitted by the luminescent material is detected at selected wavelengths such as those marked A, B and C in FIG. 1. The relative intensities at these selected wavelengths are compared and the comparison can provide an indication of the nature of the luminescent material under test or whether or not it is a particular luminescent material that is being searched for in the test. By comparing the relative intensities at the selected wavelengths, the results obtained are independant of the overall intensity level of the emitted radiation. In this way, variation in the excitation radiation used or any other variable factors such as the precise location or quantity of luminescent material or changes in the optical detection systems used may cause variation in the overall intensity of emitted radiation but will have no affect on the relative magnitudes of the intensities and the selected wavelengths.

A first optical arrangement which may be used to carry out the invention is shown in FIG. 2. In this case an article under test is shown as a sheet of paper or cardboard marked 11. The article is arranged to carry on its upper surface a selected area of luminescent material having a characteristic emission spectrum. A source 12 is arranged to provide excitation radiation which is directed through a filter 13 arranged to direct radiation onto a selected area of the article under test below a light pipe 27. In this particular case the source of radiation 12 is a low pressure mercury lamp with a phosphor coated envelope providing broad ultraviolet light centered at about 350 nm. The filter 13 is provided to isolate the ultraviolet light and reject the mercury emission lines in the visible region. Other light sources such as a capillary flash lamp which may be operated for example at 50 Hz may be used. When the area of luminescent material on the article 11 is positioned below the light pipe 27, the luminescent material responds to the excitation radiation by emitting luminescent radiation in all directions. Part of the emitted radiation is collected by the light pipe 27 which transmits the radiation through three separate optical systems to respective photomultipliers 18, 19 and 20 each having their associated filters 21, 22 and 23. The three separate optical systems which transmit light simultaneously to the photodetectors from the luminescent material in this case comprise separate bundles of optical fibres 24, 25 and 26. Each of the bundles of fibres 24, 25 and 26 contains an equal number of fibres, the outer ends of the fibres terminating at the respective filter. At the other end the fibres from each bundle are all intermingled with an even distribution at an interface with the common light pipe 27. In this case the light pipe 27 comprises a solid block of transparent material such as glass or plastics material having tapered sides as shown in FIG. 2 so that the end of the light pipe adjacent the article 11 is substantially wider than the other end which forms an interface with the fibre ends. The light pipe is tapered as shown so that the pipe collects light over a substantial area of the article under test and due to total internal reflection delivers the emitted light to the fibre ends. The light pipe 27 is similar to that used in FIGS. 5 and 6 and as can be seen from FIG. 6, two side faces of the light pipe are parallel to each other. The use of a light pipe avoids the fibres collecting extraneous radiation and furthermore provides uniform light intensity for all the fibre ends. As can be seen from FIG. 3, the fibres of each of the bundles are arranged to have an equal spacial distribution at the interface with the end of the light pipe 27. In FIG. 3 the fibres have been allocated reference numerals corresponding to the reference number used for the particular bundle of which the fibres form a part.

The filters 21, 22 and 23 are band pass filters selected so that their transmittances do not overlap to any substantial degree and the transmission maximum of one filter corresponds approximately to a maximum on the luminescence emission spectral curve of the luminescent material whilst the transmission maxima of the other two filters correspond to any other suitable wavelengths in the spectrum of the luminescent material and preferably are chosen to lie one on either side of the emission maxima to which one filter approximately corresponds. This is illustrated in FIG. 1 where the three filters may be chosen to correspond to the wavelengths A, B and C respectively.

The photodetectors 18, 19 and 20 each provide an electrical output signal which varies linearly in level in accordance with the intensity of the emitted radiation incident thereon. The electrical outputs of the three photodetectors are coupled to a control circuit which may be of the type shown in FIG. 4 and which will be described hereinbelow. The control circuit is arranged to modify by attenuation or amplification the signal from one of the photodetectors and compare the modified signal levels with the signal levels derived from the other two photodetectors. The results of the comparison are used to determine whether the luminescent material under test is a particular luminescent material that is being looked for or whether the luminescent material is one of a selected number of possible luminescent materials.

The control circuits used in conjunction with the embodiment shown in FIG. 2 is illustrated in FIG. 4. The photodetectors 18, 19 and 20 each comprise a photomultiplier having electrical outputs 28, 29 and 30 respectively. The signal level derived from each amplifier can be controlled by an associated gain control 31 coupled to the output of each photomultiplier. Each photomultiplier has an associated peak follower circuit 32 which acts as an amplifier for the output of the associated photomultiplier and rectifies the AC component of the output signal of the photomultiplier. In this way DC output voltage signals are obtained on lines 33, 34 and 35 which are representative of the intensity of illumination detected by the respective photomultiplier. In this particular case the signal 28 corresponds to that for the wavelength marked A in FIG. 1, the signal 29 corresponds to the intensity at wavelength B and the signal 30 corresponds to the intensity detected for wavelength C. The relative intensities derived at wavelengths A, B and C are known by prior calibration using a reference material and the apparatus of the example is being used to check whether the article under test has a luminescent material which corresponds to that previously used during calibration. It is therefore expected that if the material under test is the luminescent material previously used in calibration, the signal 28 will be larger than signals 29 and 30 as the intensity of the wavelength detected by the photomultiplier 18 should be the greatest. Consequently the signal on line 33 is applied to a potentiometer 36 which provides an output 37 which is a selected fraction of the voltage level on line 33. The reduced output signal 37 is itself applied to a further potentiometer 38 to provide a further reduced output signal 39. A comparator 40 has two inputs, one connected to the signal 37 and the other to line 34. The output of the comparator 40 is connected to a light emitting diode 41 and to an AND gate 42. The comparator is arranged so that the diode 41 will light up if the signal on line 34 is less than the attenuated signal 37 derived from the photomultiplier output 28. A further comparator 43 has one input connected to line 34 and a second input arranged to receive the second attenuated signal 39. The output of comparator 43 is connected to a light emitting diode 44 and to the AND gate 42. The comparator 43 is arranged so that the diode 44 lights up if the signal on line 34 is greater than the second attenuated signal 39. By use of the comparators 40 and 43 two attenuated signals derived from the output of a photomultiplier 18 are compared with the output of the photomultiplier 19 and the light emitting diodes 41 and 44 provide an indication of the relative magnitude of the signals from the photomultipliers 18 and 19. Similar additional circuitry is provided to make a similar comparison between the output signal 28 and the output signal 30 derived from the photomultiplier 20. The signal on line 33 is fed to a potentiometer 45 giving a first attenuated output signal 46. The attenuated output signal 46 is itself fed to a potentiometer 47 giving rise to a second attenuated output 48. The attenuated outputs 46 and 48 are fed respectively to inputs of additional comparators 49 and 50 each arranged to receive as its other input the unmodified signal on line 35. Each of the comparators 49 and 50 is connected to the AND gate 42 and they have respective light emitting diodes 51 and 52 in their output circuits. In this way the light emitting diode 51 lights up if the attenuated signal 46 is greater than the signal on line 35 and the light emitting diode 52 lights up if the signal on line 35 is greater than the second attenuated signal 48. The AND gate 42 is connected to a light emitting diode 53 which is arranged to light up if the outputs of all four comparators 40, 43, 49 and 50 indicate that the luminescent material under test has relative intensities at the wavelengths A, B and C which agree with those for the reference material used when calibrating the apparatus. If for any reason the luminescent material found on the article under test does not agree with that previously used when calibrating the apparatus, the relative magnitudes of the photomultiplier signals corresponding to the wavelengths A, B and C will not be such as to satisfy the comparators 40, 43, 49 and 50 and consequently some of the light emitting diodes will not illuminate. Line 33 which has the strongest output signal is connected to an overload device 55 which comprises a comparator fed with a suitable reference input 56. The output of the overload device is connected to a light emitting diode 57 so that a warning signal may be given if the output from the photomultiplier 18 is too high.

It will be appreciated that the settings of the potentiometers 36, 38, 45 and 47 are derived by prior calibration of the apparatus using a reference luminescent material and this may be varied from time to time when the apparatus is used to search for different types of luminescent material. Furthermore, although the examples described use three photodetectors with a corresponding number of components in the control circuit, more than three may be used with corresponding additional potentiometers and comparators in the control circuits. An increase in the number of photodetectors increases the certainty of identification of the material under test. It also can increase the versatility of the apparatus. For example, if two fluorescent materials have emission curves which in part coincide and in part differ, the apparatus may be used to distinguish between the two and indicate the presence or absence of either.

FIGS. 5 and 6 show a further alternative optical arrangement. This is generally similar to the arrangement shown in FIG. 2 in using photodetectors 18, 19 and 20 each having an associated bundle of light fibres 24, 25 and 26 leading to a common light pipe 27. However, in the case of FIG. 2 the source of excitation radiation was a single excitation source (not shown) whereas in FIGS. 5 and 6 the excitation source consists of two lamps arranged on each side of the light pipe 27. Each lamp 12 extends along a horizontal casing 60 having an inclined elongated window 61 facing down towards the article 11. The light pipe 27 passes vertically between the two adjacent edges of the lamp housing 60 and the lower edge of the light pipe projects downwardly below the lamp housings.

In both FIGS. 2 and 5 it is possible to modify the apparatus to avoid the use of the light pipe. In this case the ends of the fibres themselves will terminate shortly above the article under test and the fibre ends will then have the uniform distribution shown in FIG. 3 immediately above the article under test. One arrangement of this type is shown in FIG. 7 in combination with an alternative way of supplying excitation radiation. In this case each of the photodetectors 18, 19 and 20 has its associated fibre bundle 24, 25 and 26 with the ends of the fibres terminating shortly above the article 11. However, in this case the ends of the detection fibres are uniformly distributed in an annular form around an additional bundle of fibres providing the excitation radiation. This additional bundle of fibres marked 62 forms a central core of fibres surrounded by the detection fibres 24, 25 and 26 at their ends facing the article 11. The bundle 62 is connected to a light pipe 63 generally similar to the light pipe 27 previously described. In this case the broader end of the light pipe faces a light source 12 provided with a suitable filter 64.

Figure 8:
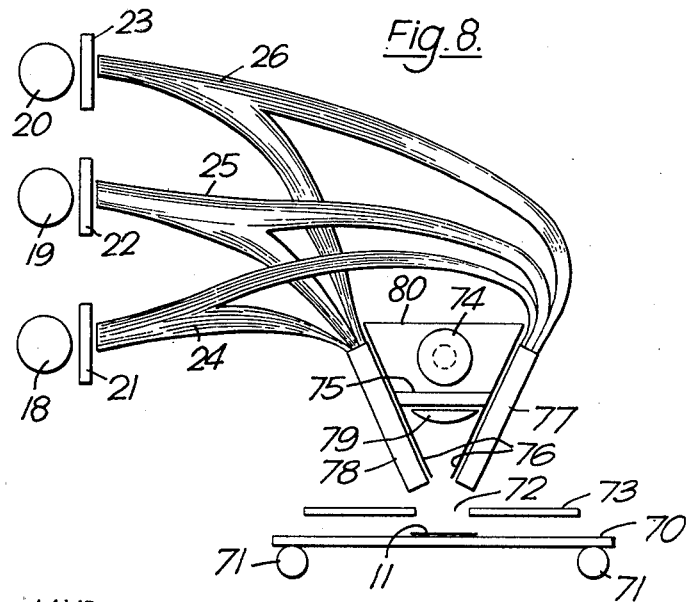
FIG. 8 shows a preferred embodiment of the invention.
Figure 9:
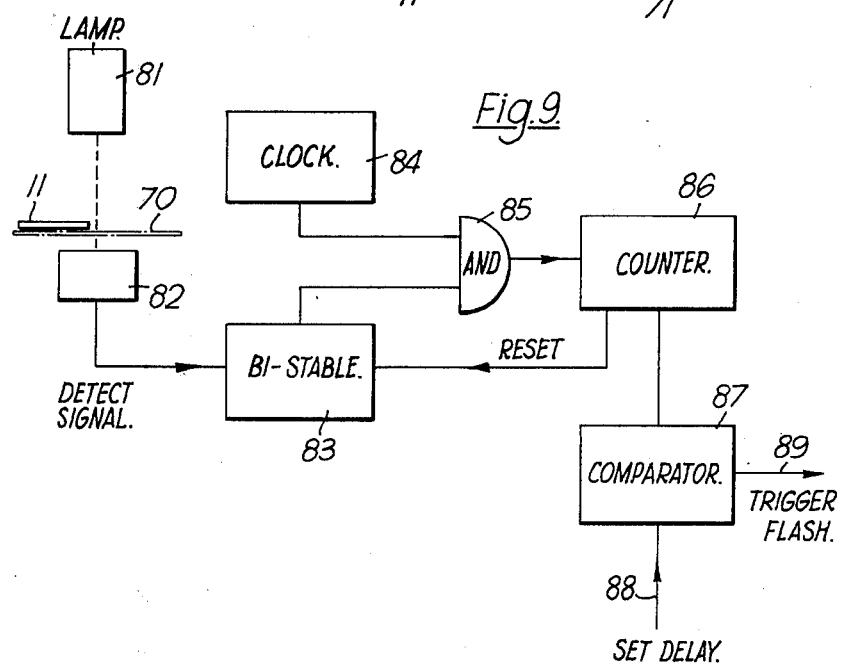
FIG. 9 shows a control circuit for use with the apparatus of FIG. 8.

It is desirable in some cases to test articles which are being conveyed by a conveying system. A preferred embodiment of the invention arranged for this purpose is shown in FIGS. 8 and 9. In this case the articles under test are conveyed on a conveying system 70 having motor driven rollers 71. The conveying system is arranged to pass below a slit aperture 72 in a plate 73. Mounted in a housing 76 above the aperture is a flash lamp 74 providing a source of excitation radiation. An ultraviolet filter 75 and cylindrical lens 79 are located immediately below the lamp 74. Light passing through the filter is directed by the lens 79 through a lower open end of the housing 76 towards the slit aperture 72. Mounted adjacent the exterior of the housing 76 are two light pipes 77 and 78 similar to the light pipe 27 previously described. Each of the light pipes 77 and 78 is connected to the bundles of fibres 24, 25 and 26 leading to the photodetectors 18, 19 and 20. The fibres of each bundle are split into two groups, one group connected to the pipe 77 and the other group connected to the pipe 78. Each group contains an even distribution of fibres from each of the bundles. The light pipes 77 and 78 are inclined to the vertical so that the lower faces of the two light pipes are directed at the conveyor surface below the slit 72. The length of the light pipe apertures runs parallel to the length of the slit 72 and this is transverse to the direction of movement of the conveyor 70. The flash lamp 74 is coupled to a control circuit arranged to synchronise the operation of the flash lamp with the arrival of each article at the test station whereby a short duration flash is directed at the article under test while it is moving on the conveyor, thereby apparently freezing the movement of the article. The operation of the device is otherwise similar to that previously described. The synchronisation of the lamp 74 with the arrival of each article will now be described with reference to FIG. 9.

The area of fluorescent material on the article under test is preferably kept as small as possible so that the light pipes 77 and 78 detect only fluorescent material which passes through the aperture 72. The area of the fluorescent material may be slightly larger than the area of the aperture 72 but accurate synchronisation of operation of the flash lamp 74 is necessary to achieve satisfactory operation. In the arrangement shown in FIG. 9, the article 11 under test is shown moving along the conveyor path 70 between a lamp 81 and light detector 82. This is mounted at a convenient position in relation to the apparatus shown in FIG. 8 so that the detector 82 can detect the edge of the article as the article approaches the test station. When the edge of the article arrives at a predetermined position the light normally detected by the detector 82 is interrupted and this provides a signal to a bistable 83. The output of the bistable is fed together with the output of a crystal controlled clock 84 into an AND gate 85. The output of the AND gate is fed to a counter 86 which is arranged to provide a reset signal to the bistable 83. The counter 86 is also coupled to a comparator 87 which is fed with an adjustable delay signal on line 88. The comparator is arranged to provide an output pulse on line 89 for use in triggering the flash lamp 74. The output pulse on line 89 is thereby operated at a precisely fixed time delay after detection of the edge of the article 11 and the whole operation is maintained at precisely fixed timing by the clock 84.

In this way, the article may be arranged to travel at high speed, such as for example 250 inches per second and the flash may be operated with a delay of 14 ms after the position of the article is detected by the detector 82.

As an alternative to use of the lamp 81 and photodetector 82, the position of the article approaching the test station may be detected by using a single light pipe and a photodetector to detect the fluorescence on the article. The detector can be used to determine when the fluorescence exceeds a certain value. In this case, the light pipe may be positioned adjacent one edge of the aperture 72 and light from the pipe delivered to a detector in place of the detector 82 in FIG. 9.

It will be appreciated that the invention is not limited to the details of the foregoing examples. Various changes may be made in the light source and the number of photodetectors used as well as the control circuit used for comparing the outputs of the photomultipliers. Furthermore, the invention may be used for a variety of purposes. The invention is particularly applicable to the examination of labels for pharmaceutical products as well as checking and sorting containers to which suitable labels are fixed when the containers are being transported, sorted or packed. Furthermore, a variety of articles incorporating luminescent materials may be examined and/or sorted by use of the apparatus and methods described above.

I claim:

1. Apparatus for characterising an article which is provided with luminescent material, which apparatus comprises a source of excitation radiation for directing radiation at the luminescent material when the article is at a test station, a plurality of optical systems arranged to receive simultaneously radiation emitted by the luminescent material and direct the radiation to respective photodetectors, a plurality of optical filters each arranged with a different wavelength transmission and each being located in a respective one of the optical systems and arranged to pass radiation to the associated photodetector, and electrical circuit means arranged so as:
   (1) to receive electrical output signals derived from said photodetectors said signals varying linearly in level in accordance with the intensity of radiation incident thereon;
   (2) to effect comparison of signals derived from the respective photodetectors in order to characterise the article;
   (3) to provide at least one pair of signal levels defining a desired range for use in determining whether the comparison falls within a desired range, and
   (4) to provide an output signal indicating the result of the comparison.

2. Apparatus for characterising an article which is provided with luminescent material, which apparatus comprises a source of excitation radiation for directing radiation at the luminescent material when the article is at a test station, a plurality of optical systems arranged to receive simultaneously radiation emitted by the luminescent material and direct the radiation to respective photodetectors, a plurality of optical filters each arranged with a different wavelength transmission and each being located in a respective one of the optical systems and arranged to pass radiation to the associated photodetector, and electrical circuit means arranged so as:
   (1) to receive electrical output signals derived from said photodetectors said signals varying linearly in level in accordance with the intensity of radiation incident thereon;
   (2) to modify the signal level from one photodetector to provide at least one pair of different modified signals serving to define a required range;
   (3) to compare a signal level derived from each other photodetector with a pair of modified signal levels, and
   (4) to indicate when the signal level derived from each other detector is within the required range.

3. Apparatus for characterising an article which is provided with luminescent material, which apparatus comprises a source of excitation radiation for directing radiation at the luminescent material when the article is at a test station, a plurality of optical systems arranged to receive simultaneously radiation emitted by the luminescent material and direct the radiation to respective photodetectors, a plurality of optical filters each arranged with a different wavelength transmission and each being located in a respective one of the optical systems and arranged to pass radiation to the associated photodetector, and electrical circuit means arranged so as (1) to receive electrical output signals derived from said photodetectors, said signals varying linearly in level in accordance with the intensity of radiation incident thereon; (2) to modify the signal level from one photodetector to provide two different modified signal levels serving to define a required range; (3) to compare a signal level derived from another photodetector with each of the modified signal levels and (4) to indicate when said signal level derived from said other photodetector is within said required range.

4. Apparatus according to claim 3, wherein the optical systems each comprise a plurality of optical fibres.

5. Apparatus according to claim 4, wherein said optical systems each comprise a bundle of optical fibres, each bundle having one end arranged to direct light to a respective photodetector and the other ends of the fibres forming one or more groups, the or each group having fibres lying closely adjacent each other in a common plane and distributed so that fibres of all bundles have an even distribution at the end arranged to receive radiation from the article under test.

6. Apparatus according to claim 5, wherein at least one light pipe is provided for receiving radiation emitted by the luminescent material and directing the radiation to one end of the bundles of fibres.

7. Apparatus according to claim 6, wherein the fibres of all said bundles are connected at one end to one or more light pipes common to all the bundles, the fibres of the different bundles having an even distribution at the interface with the or each light pipe.

8. Apparatus according to claim 5 wherein the source of excitation radiation comprises a radiation source located adjacent at least the end of the fibre bundles arranged to receive radiation emitted by the luminescent material.

9. Apparatus according to claim 5 wherein the bundles of fibres are connected to two light pipes spaced apart and incident to each other so as to detect radiation from the same part of an article under test, the source of excitation radiation being arranged to direct radiation onto the article along a path symmetrically disposed between the two light pipes.

10. Apparatus according to claim 3, wherein the source of excitation radiation is an ultra violet source.

11. Apparatus according to claim 10, wherein the source of excitation radiation comprises a flash lamp.

12. Apparatus according to claim 11 wherein conveyor means is provided for moving a succession of articles past a test station and the apparatus includes detector means for detecting the arrival of an article at the test station and synchronising means is provided to synchronise the operation of the flash lamp with the arrival of the article at the test station.

13. Apparatus for characterising an article which is provided with luminescent material, which apparatus comprises a source of excitation radiation for directing radiation at the luminescent material when the article is at a test station, three optical systems arranged to receive simultaneously radiation emitted by the luminescent material and direct the radiation to respective photodetectors, three optical filters each arranged with a different wavelength transmission and each being located in a respective one of the optical systems and arranged to pass radiation to the associated photodetector, and electrical circuit means arranged so as:

(1) to receive electrical output signals derived from said photodetectors said signals varying linearly in level in accordance with the intensity of radiation incident thereon;
(2) to modify the signal level from a first photodetector to provide two pairs of different modified signal levels to define first and second required ranges;
(3) to compare a signal level derived from the second photodetector with the first required range;
(4) to compare a signal level derived from the third photodetector with the second required range; and
(5) to generate an acceptance signal when the signal levels derived from the second and third photodetectors are within said first and second required ranges, respectively.

14. A method of characterising an article which is provided with luminescent material, which method comprises directing excitation radiation at the luminescent material on an article under test so as to cause the luminescent material to emit luminescent radiation, detecting the emitted radiation at different wavelengths by simultaneously directing said radiation through a plurality of optical systems to respective photodetectors, each optical system incorporating filter means having a selected wavelength transmission to its associated photodetector, the selected wavelengths transmission differing from that of another optical system, and each photodetector giving rise to an output signal which varies linearly in level in accordance with the intensity of the emitted radiation incident thereof, modifying the signal level from one photodetector to provide at least one pair of different modified signals serving to define a required range, comparing a signal level derived from each other photodetector with a pair of modified signal levels, and determining when the signal level derived from each other detector is within the required range.

* * * * *